United States Patent
Dai et al.

(10) Patent No.: US 9,636,324 B2
(45) Date of Patent: May 2, 2017

(54) USE OF 15-BENZYLIDENCE-14-DEOXY-11, 12 -DEHYROANDROGRAPHOLIDE DERIVATIVE IN MANUFACTURE OF MEDICAMENTS FOR PROTECTING LIVER AND ANTI-HEPATITIS C VIRUS

(71) Applicant: Zhengzhou University, Zhengzhou (CN)

(72) Inventors: Guifu Dai, Zhengzhou (CN); Jing Zhao, Zhengzhou (CN); Haiwei Xu, Zhengzhou (CN); Huanfei Liu, Zhengzhou (CN); Zhenwei Wu, Zhengzhou (CN); Di Wu, Zhengzhou (CN); Jian Wu, Zhengzhou (CN); Hongmin Liu, Zhengzhou (CN)

(73) Assignee: Zhengzhou University, Zhengzhou (CN)

( * ) Notice: Subject to any disclaimer, the term of this patent is extended or adjusted under 35 U.S.C. 154(b) by 0 days.

(21) Appl. No.: 15/176,354

(22) Filed: Jun. 8, 2016

(65) Prior Publication Data

US 2016/0279096 A1    Sep. 29, 2016

Related U.S. Application Data

(63) Continuation of application No. 14/377,386, filed as application No. PCT/CN2013/071357 on Feb. 5, 2013, now Pat. No. 9,388,169.

(30) Foreign Application Priority Data

Feb. 10, 2012  (CN) .......................... 2012 1 0029633
Feb. 10, 2012  (CN) .......................... 2012 1 0029634

(51) Int. Cl.
| | | |
|---|---|---|
| *A61K 31/34* | (2006.01) |
| *A61K 31/365* | (2006.01) |
| *A61K 31/443* | (2006.01) |
| *A61K 9/00* | (2006.01) |
| *C07D 307/33* | (2006.01) |
| *C07D 307/58* | (2006.01) |
| *C07D 405/12* | (2006.01) |
| *A61K 31/455* | (2006.01) |
| *A61K 47/38* | (2006.01) |

(52) U.S. Cl.
CPC .......... *A61K 31/365* (2013.01); *A61K 9/0019* (2013.01); *A61K 9/0053* (2013.01); *A61K 31/443* (2013.01); *A61K 31/455* (2013.01); *C07D 307/33* (2013.01); *C07D 307/58* (2013.01); *C07D 405/12* (2013.01); *A61K 47/38* (2013.01)

(58) Field of Classification Search
CPC .................................................... C07D 405/12
USPC ........................................................ 514/474
See application file for complete search history.

(56) References Cited

FOREIGN PATENT DOCUMENTS

| | | |
|---|---|---|
| CN | 101416958 | 4/2009 |
| CN | 102302487 | 1/2012 |
| CN | 102526026 | 7/2012 |
| CN | 102600129 | 7/2012 |
| WO | WO2006101538 | 9/2006 |

OTHER PUBLICATIONS

Xu et al., Bioorganic & Medicinal Chemistry (2007), 15(2), 8 pages.
Durantel et al., Current Opinion in Investigational Drugs (Thomson Scientific) (2007), 8(2), 5 pages.
International Search Report dated May 16, 2013; International Application No. PCT/CN2013/071357; International Filing Date: Feb. 5, 2013; 5 pages.
English translation of International Search Report dated May 16, 2013; International Application No. PCT/CN2013/071357; 3 pages.
English abstract; Chinese Application No. CN102600129; 1 page.
English abstract; Chinese Application No. CN102526026; 1 page.
English abstract; Chinese Application No. CN102302487; 1 page.
Written Opinion dated May 16, 2013; International Application No. PCT/CN2013/071357; 6 pages.
English translation of Written Opinion dated May 16, 2013; International Application No. PCT/CN2013/071357; 8 pages.

Primary Examiner — Nizal Chandrakumar
(74) Attorney, Agent, or Firm — Blank Rome LLP

(57) ABSTRACT

Disclosed is use of andrographolide derivative as shown by general formula 1 in manufacture of medicaments for anti-hepatitis C virus, and preventing and treating immunological liver damage caused by virus infection and different chemical liver damage.

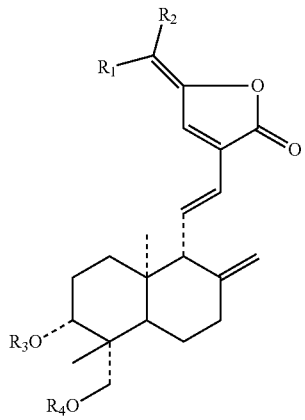

Formula 1

6 Claims, 9 Drawing Sheets

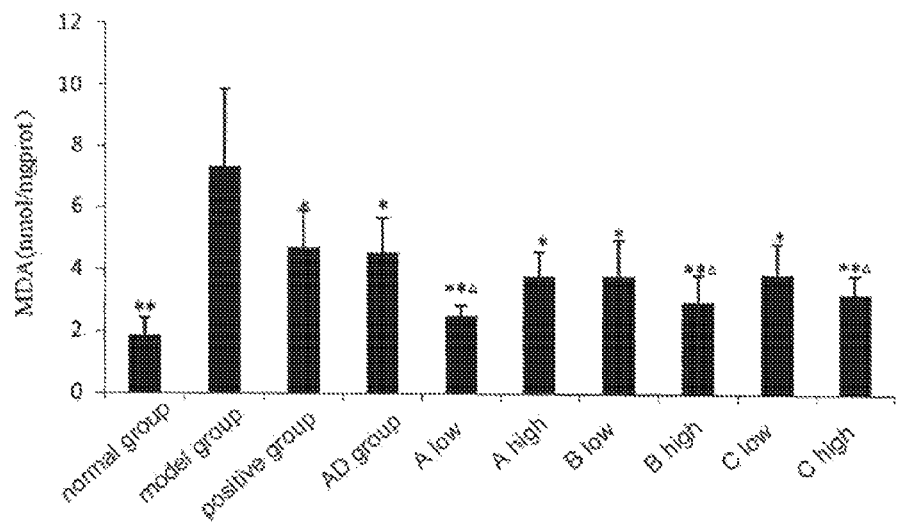
FIG. 3
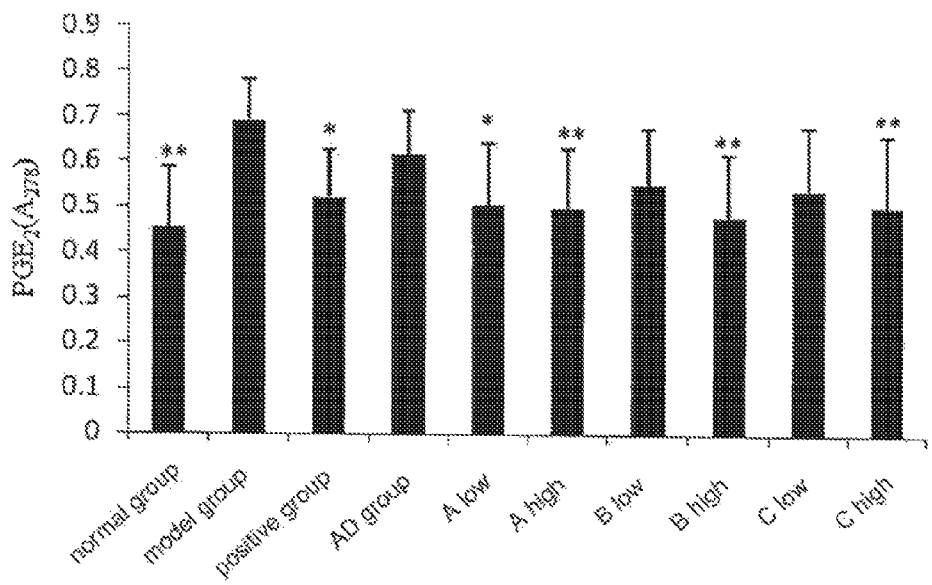
FIG. 4
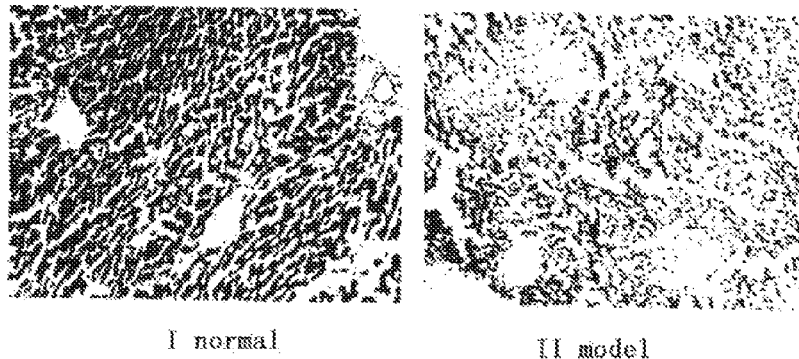

USE OF 15-BENZYLIDENE-14-DEOXY-11, 12-DEHYROANDROGRAPHOLIDE DERIVATIVE IN MANUFACTURE OF MEDICAMENTS FOR PROTECTING LIVER AND ANTI-HEPATITIS C VIRUS

RELATED APPLICATIONS

This application is a continuation of U.S. application Ser. No. 14/377,386, filed Aug. 7, 2014; which application is a U.S. National Stage of International Application No. PCT/CN2013/071357, filed Feb. 5, 2013; which application claims benefit of priority of China Application No. 2012 10029633.6, filed Feb. 10, 2012 and China Application No. 2012 10029634.0, filed Feb. 10, 2012. Each of the above-identified related applications are incorporated herein by reference.

FIELD OF THE INVENTION

The present invention relates to the medical use of andrographolide derivatives, particularly relates to the hepatoprotective activity and antiviral activity of 15-benzylidene-14-deoxy-11,12-dehydroandrographolide derivatives, and belongs to the field of pharmaceutical technology.

BACKGROUND OF THE INVENTION

Hepatic disease is a world-wide common and frequently-happening disease. Liver damage is caused by invasion of extraneous factors such as virus, organisms, medications, physical and chemical factors, alcohol and the like. There are more than 280 million silent hepatitis B (HBV) carriers (HBsAg carriers) in the world and around 93 million in our country. About 30% of HBV carriers show clinical manifestation of liver damage. Hepatitis C virus (HCV) infection is a common infection which can lead to chronic hepatitis, hepatocirrhosis, hepatic failure and hepatocellular carcinoma, and at least 85% of the HCV infection cause chronic hepatitis. It is found by investigation that same as HBV, HCV's tissue infiltrating cell is primarily CD3+ and cytotoxic T cells (TCL) specifically attack target cell infected by HCV, causing hepatocellular damage.

At present, effective anti-HCV therapy is still limited to interferon therapy or its combined therapy with ribavirin, and vaccines which can effectively prevent HCV have not been developed. However, since about half of the patients treated with these known medications show remaining HCV inside their bodies, there is still a strong demand for alternative HCV medicaments. HCV is the only member of the Hepaciviruses of the Flaviviridae family. Bovine viral diarrhea virus (BVDV) is a virus of Flavivirus genus of the Flaviviridae family and has the same antigen as HCV. It's impossible to steadily culture HCV externally to date, but BVDV can easily grow in Madin Darby bovine kidney (MDBK) cell and its gene coding product can be easily obtained and thus is convenient for use in genomic research. BVDV AV69 (NADL) strain can cause pathological change in cells, so that the antiviral activity of a medicament could be assessed by using the rate of protection against pathological changes. Since the medicaments which can inhibit BVDV replication in cells could be used to treat HCV infection, BVDV has been used in HCV medicament screening extensively as a simulation strain of HCV.

Andrographolide is a diterpene lactone compound extracted from *Andrographis paniculata* (Burm.f.) Nees, is one of the major active components of *Andrographis paniculata* and is clinically used in the treatment of upper respiratory tract infection and bacillary dysentery and the like. In recent years, the investigation of use of andrographolide in anticancer, liver and gallbladder protection, antivirus and the like is continuously progressing. Andrographolide has excellent protective effect against several animal experimental liver damages. Qing Yao et al. found andrographolide had some protective effect against acute liver damage induced by cocaine, and the mechanism might relate to inhibition of lipid peroxidation and lowering the production of oxygen free radical in tissue. Visen P K [J Ethnopharmacol, 1993, 40(2), 131-136] and Handa S [Indian J Med Res., 1990, 92:284-292] both proved andrographolide had protective effect against liver damage induced by paracetamol, wherein Handa S's work also proved the protective effect against hepatotoxicity caused by galactosamine. Kapil A et al. [Biochem Pharmacol, 1993, 46(1):182-185] proved andrographolide, andrographoside and neoandrographolide had protective effect against hepatotoxicity caused by carbon tetrachloride and t-butyl peroxide. The study of Singha P et al. [J Ethnopharmacol. 2007; 111(1):13-21] showed andrographolide had some protective effects against kidney and liver damage caused by ethanol in mice. The study of Roy D N et al. [Toxicol Appl Pharmacol. 2011; 250(1): 54-68] proved combination of andrographolide and D-green enzyme amine in treatment of copper poison had better effect than single use of D-green enzyme amine in treatment of anti-fibrillation and necrocytosis. Guang Ning et al. disclosed in their application CN201010266185.2 the use of andrographolide in preparation of a medicament for treatment of acute liver damage, and that andrographolide can significantly suppress liver damage and liver cell apoptosis induced by concanavalin A and suppress the inflammation reaction of liver, and thus, it can be used to treat liver damage induced by concanavalin A.

As revealed by experiments, andrographolide and its derivatives had excellent prospective for use in anti-flavivirus, anti-pestivirus or anti-hepatitis C virus applications (CN: 200580046253.1) and anti-SARS virus applications (CN: 03129127.9). Combination of ingredients of herba andrographitis with other plants or the ingredients thereof has antiviral activity. (U.S. Pat. No. 5,833,994) disclosed the combination of andrographolide with an arene ligand in treatment of virus infection. Andrographolide succinic acid monoester inhibited HIV by interrupting its binding with cells and by interfering with its replication cycle till subsequent stage of its binding with cells. Methanol extract of *Andrographis paniculata* could inhibit HIV-1 in vitro replication by inhibiting c-Mos.

The inventors have obtained a lot of structurally novel compounds in previous studies (CN1978437; CN100999520; CN100999535; CN101003527), for which compounds patent protections on their anticancer, anti-inflammatory and anti-HBV applications are sought for. Then, activity tests of the anti-HCV and hepatoprotective effects of 15-benzylidene-14-deoxy-11, 12-dehydroandrographolide derivatives and the 3, 19-ester thereof are further conducted.

SUMMARY OF THE INVENTION

Based on previous research, with screening of the synthesized compounds for their anti-HCV and hepatoprotective activities, the inventors find that andrographolide derivatives with the Formula (I) have significant effects on prevention and treatment of liver damage. Some compounds can notably suppress MDBK cytopathy induced by BVDV, with high efficiency and low toxicity, and thus have the potential to be developed as an anti-HCV drug. The present invention is intended to provide use of a 15-benzylidene-14-deoxy-11,12-dehydroandrographolide derivative in the preparation of a hepatoprotective and anti-HCV drug.

A 15-benzylidene-14-deoxy-11,12-dehydroandrographolide derivative of the invention has the structure as shown in Formula 1:

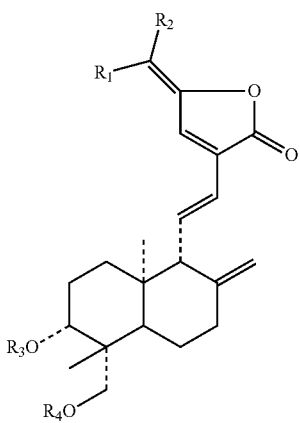

Formula 1 wherein $R_1$ is hydrogen; $R_2$ is phenyl, 4-fluorophenyl, 4-chlorophenyl, 4-bromophenyl, 3-fluorophenyl, 3-chlorophenyl, 3-bromophenyl; $R_3$ and $R_4$ are each independently hydrogen or $COR_5$, of which $R_5$ is 3-pyridyl or $CH_2CH_2COOH$.

The above compounds have hepatoprotective activities, wherein preferably, $R_1$ is hydrogen; $R_2$ is 4-fluorophenyl, 4-chlorophenyl, 4-bromophenyl, 3-fluorophenyl, 3-chlorophenyl, 3-bromophenyl; $R_3$ and $R_4$ are each independently hydrogen or $COR_5$, of which $R_5$ is 3-pyridyl or $CH_2CH_2COOH$.

The preferred compounds are particularly as follows:
A: $R_1$=H, $R_2$=4-Cl—$C_6H_4$, $R_3$=$R_4$=H;
B: $R_1$=H, $R_2$=$C_6H_5$, $R_3$=$R_4$=H;
C: $R_1$=H, $R_2$=3-Br—$C_6H_4$, $R_3$=$R_4$=H;
D: $R_1$=H, $R_2$=4-Cl—$C_6H_4$, $R_3$=$R_4$=$COR_5$, $R_5$=3-pyridyl;
E: $R_1$=H, $R_2$=4-Cl—$CH_4$, $R_3$=$R_4$=$COR_5$, $R_5$=$CH_2CH_2COOH$;

Among them, compounds also having anti-HCV activity are those wherein $R_1$ is hydrogen; $R_2$, is phenyl, 4-fluorophenyl, 4-chlorophenyl, 4-bromophenyl; $R_3$ and $R_4$ are each independently hydrogen or $COR_5$, of which $R_5$ is 3-pyridyl or $CH_2CH_2COOH$.

The preferred anti-HCV compounds are those wherein $R_1$ is hydrogen; $R_2$ is 4-fluorophenyl, 4-chlorophenyl, 4-bromophenyl; $R_3$ and $R_4$ are each independently hydrogen or $COR_5$, of which $R_5$ is 3-pyridyl or $CH_2CH_2COOH$.

More preferred anti-HCV compounds are particularly as follows:
A: $R_1$=H, $R_2$=4-Cl—$C_6H_4$, $R_3$=$R_4$=H;
D: $R_1$=H, $R_2$=4-Cl—$C_6H_4$, $R_3$=$R_4$=$COR_5$, $R_5$=3-pyridyl;
E: $R_1$=H, $R_2$=4-Cl—$C_6H_4$, $R_3$=$R_4$=$COR_5$, $R_5$=$CH_2CH_2COOH$.

The preparation method of the compounds of this invention mentioned above has been made public in the previous patent (CN: 200510107247.4). In this method, 14-deoxy-11,12-dehydroandrographolide or one of the 3,19-ester derivatives of 14-deoxy-11,12-dehydroandrographolide and a kind of aldehyde are dissolved in methanol, ethanol or tetrahydrofuran, and then an andrographolide derivative shown in Formula 1 can be obtained through heating the mixture at a temperature of 15 to 70° C., catalyzed by a base at 0.2-5% mol, wherein the base used is one of sodium carbonate, potassium carbonate, sodium bicarbonate, triethylamine, pyridine, N,N-dimethylaminopyridine, and the aldehyde used is an aromatic aldehyde, preferably, benzaldehyde, halogenated benzaldehyde or the like, and more preferably, p-fluoro-, p-chloro-, p-bromo, m-fluoro-, m-chloro- or m-bromobenzaldehyde; the ester derivatives of 14-deoxy-11,12-dehydroandrographolide used are those when $R_3$ and $R_4$ in formula 1 are both $COR_5$, of which $R_5$ is 3-pyridyl or $CH_2CH_2COOH$.

To achieve the goals of the present invention, immunological liver damage model induced by Concanavalin A (ConA) was used to investigate the effects of the 15-benzylidene-14-deoxy-11,12-dehydroandrographolide derivatives on alanine aminotransferase (ALT) and aspartate aminotransferase (AST) activity in mice serum, and the contents of lipid peroxide malondialdehyde (MDA) and inflammatory mediator prostaglandin $E_2$ ($PGE_2$) in liver homogenate. Proved by the experiments, the 15-benzylidene-14-deoxy-11,12-dehydroandrographolide derivatives of the invention could effectively reduce the aminotransferase activity in serum, suppress the production of lipid peroxide MDA, suppress the generation of inflammatory mediator $PGE_2$, and could effectively mitigate liver damage.

To achieve the goals of the present invention, MNDBK (NBL-1) cells and BVDV strain (BVDV-AV69) were used to investigate the therapeutical effect of the 15-benzylidene-14-deoxy-11,12-dehydroandrographolide derivatives of the invention on cytopathy caused by BVDV infection, and MTT assay was used to investigate the cytotoxicity of the compounds to MDBK. Proved by the experiments, such dehydroandrographolide derivatives can notably suppress MDBK cytopathy caused by BVDV and have potential of use in preparation of anti-HCV drugs.

To achieve the goals of the present invention, chemical liver damage model induced by carbon tetrachloride was also used to investigate the effects of the 15-benzylidene-14-deoxy-11,12-dehydroandrographolide derivatives on ALT and AST activity in mice serum, and MDA and $PGE_2$ content in liver homogenate. Proved by the experiments, the 15-benzylidene-14-deoxy-11,12-dehydroandrographolide derivatives could effectively reduce the aminotransferase activity in serum, and decrease the MDA, $PGE_2$ content in liver.

To achieve the goals of the present invention, liver damage model induced by ethanol was used to investigate the effects of the 15-benzylidene-14-deoxy-11,12-dehydroandrographolide derivatives on ALT and AST activity in mice serum, and on MDA content in liver homogenate. Proved by the experiments, the 15-benzylidene-14-deoxy-11,12-dehydroandrographolide derivatives could effectively reduce the aminotransferase activity in serum, and decrease the MDA content in liver.

According to conventional pharmaceutical methods and process requirements, the derivative can be used as an active ingredient, or in combination with other drug(s), and mixed with a pharmaceutically acceptable auxiliary and/or additive, to prepare an anti-HCV or hepatoprotective drug in the form of an oral or injectable preparation. The oral preparation is tablet, pill, capsule, granule or syrup; the injectable preparation includes an injection or a lyophilized powder for injection.

The advantages of the present invention: upon activity screening, the above compounds are determined to have clear in vitro anti-BVDV activity and hepatoprotective activity which are notable and better than those of the parental compound andrographolide (AD); the compounds also have high efficiency and low toxicity, providing a new path for developing medicaments for prevention and treatment of HCV and other various liver damages, and expanding the range of available clinical drugs.

BRIEF DESCRIPTION OF THE FIGURES

FIG. 3 shows comparison of test results for compound A, B, C and AD against MDA content in liver homogenate of mice with ConA induced liver damage.

FIG. 4 shows comparison of test results for compound A, B, C and AD against $PGE_2$ content in liver homogenate of mice with ConA induced liver damage.

In FIGS. 1-4, FIGS. 6-9 and FIGS. 13-23: comparing with model group: $*P<0.05$, $P<0.01$; comparing with AD group: $^{\Delta}P<0.05$, $^{\Delta\Delta}P<0.01$.

PREFERRED EMBODIMENTS OF THE INVENTION

Figure 1:
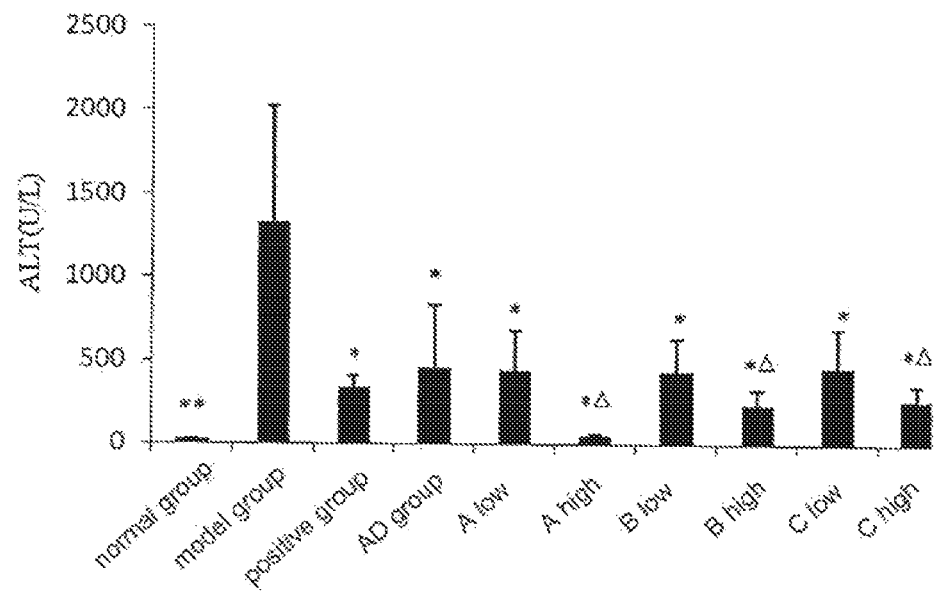
FIG. 1 shows comparison of test results for compound A, B, C and AD against ALT activity in serum of mice with ConA induced liver damage.
Figure 2:
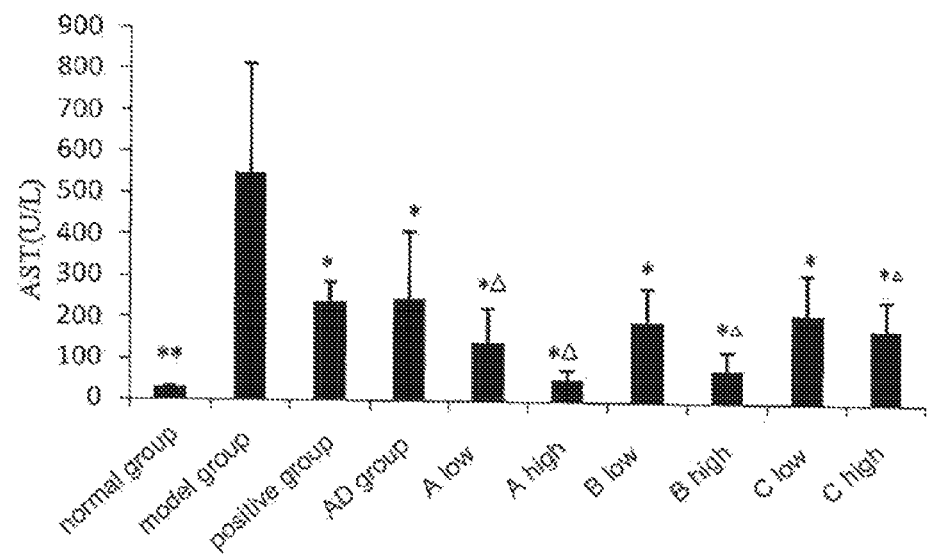
FIG. 2 shows comparison of test results for compound A, B, C and AD against AST activity in serum of mice with ConA induced liver damage.

The invention is further elaborated with preferred embodiments as follows. It should be understood that such embodiments are only for illustrating purposes and are not used to limit the scope of the present invention. Those skilled in the art can use liver damage of any cause as the research subject to establish the hepatoprotective effect of the compounds of the invention.

Example 1

In ConA Induced Immunological Liver Damage Model, Compound A, B, C and AD all Show Obvious Protective Effect Against Liver Damage 1 Experimental Methods Kunming mice of clean grade (male, weight 20±2 g, supplied by the Laboratory Animal Center, Henan Province) are randomly divided into groups with 6 mice in each group. Bifendate (Xinchang Pharmaceutical Factory of Zhejiang Pharmaceutical Co., Ltd, 200 mg/kg) is used as positive control, andrographolide (AD) is provided by Furen Pharmaceutical Group Co., Ltd, and the test compounds are synthesized by the inventors with purities higher than 99.0%. Normal control group and model group are intragastrically given 0.5% sodium carboxymethylcellulose (CMC-Na), and test groups are given 0.5% CMC-Na suspensions with AD (0.88 mmol/kg), and low dosage (0.66 mmol/kg) and high dosage (0.88 mmol/kg) of compound A, B and C, respectively. The drugs are given for 3 days. One hour after the last administration, all mice except those in the normal control group are injected with a single dose of ConA (20 mg/kg) through the caudal vein. After 8 h, the eyeball is enucleated to collect blood, which is centrifuged at 3000 rpm for 15 min to separate serum. ALT and AST are tested according to the kit specification, respectively (Nanjing Jiancheng Bioengineering Institute). The left lobe of liver is taken to prepare 10% homogenate using physiological saline, MDA is determined according to the kit specification (Nanjing Jiancheng Bioengineering Institute). To 50 µL liver homogenate is added 2 mL of 0.5 mol/L KOH-methanol solution and kept at 50° C. water bath to isomerize for 20 minutes, then absorbance (A value) is measured at 278 nm, using the A value per mL of homogenate to represent the $PGE_2$ content. Experimental data are expressed as average±standard deviation ($\bar{X}$±s), analyzed with SPSS 11.5 statistic software, with $P<0.05$ meaning significant difference.

2 Experimental Results

The effects of compound A, B, C and AD on ALT and AST activities in mice serum, and MDA and $PGE_2$ contents in liver homogenate are shown in FIGS. 1-4. As revealed by the results, comparing to AD group, each dosage group of the compounds are better than AD group to a certain extent, and the high dosage group (0.88 mmol/kg) of each compound has better enzyme lowering effect (P<0.05) comparing to AD group with the same dosage. Especially, in the high dosage group (0.88 mmol/kg) of compound A, the enzyme level essentially decreased to normal level.

AD group and different dosage groups of the compounds from the present invention all can reduce the MDA content in liver homogenate of mice with liver damage (P<0.05), especially low dosage group (0.66 mol/kg) of compound A and high dosage groups (0.88 mmol/kg) of compound B and C have more obvious effect (P<0.01). Comparing with AD group, low dosage group (0.66 mol/kg) of compound A and high dosage groups (0.88 mmol/kg) of compound B and C have stronger resistant ability against liver lipid peroxidation (P<0.01).

Compound A (high dosage, P<0.01; low dosage, P<0.05), B (high dosage, P<0.01) and C (high dosage, P<0.01) also notably reduce $PGE_2$ content in liver homogenate of mice with liver damage.

In summary, compound A, B and C have notably protective effect against immunological liver damage induced by ConA, and are better than the parent compound AD.

Figure 5:
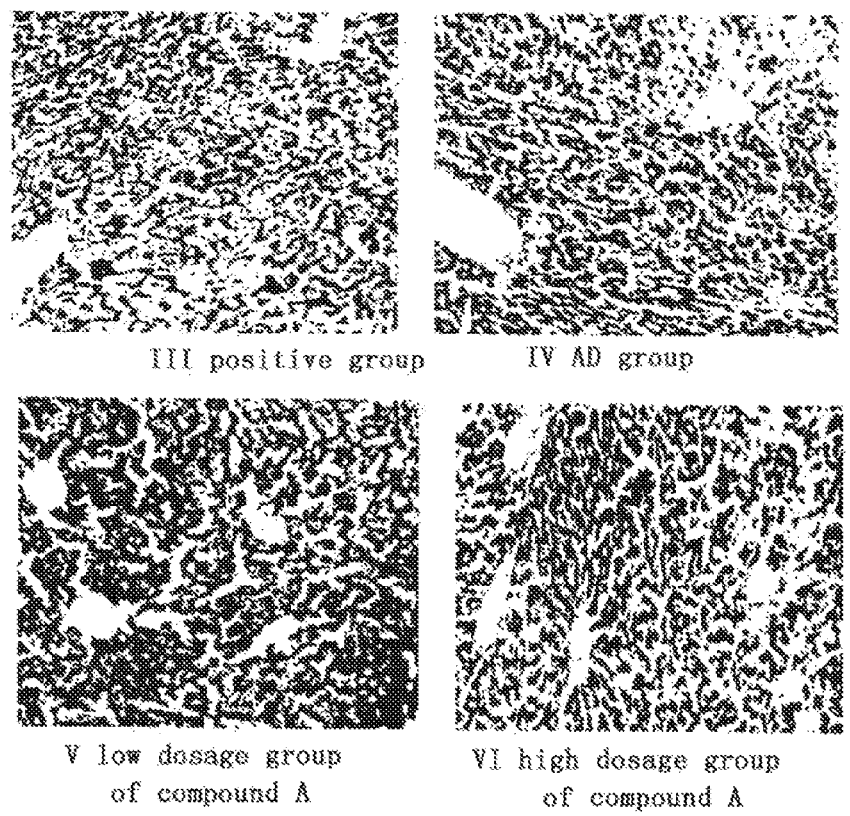
FIG. 5 shows comparison of liver histopathologic section (HE stain; 200×) test results of mice with ConA induced liver damage; in which I is normal, II is model, III is positive group, IV is AD group, V is low dosage group of compound A, VI is high dosage group of compound A.
Figure 6:
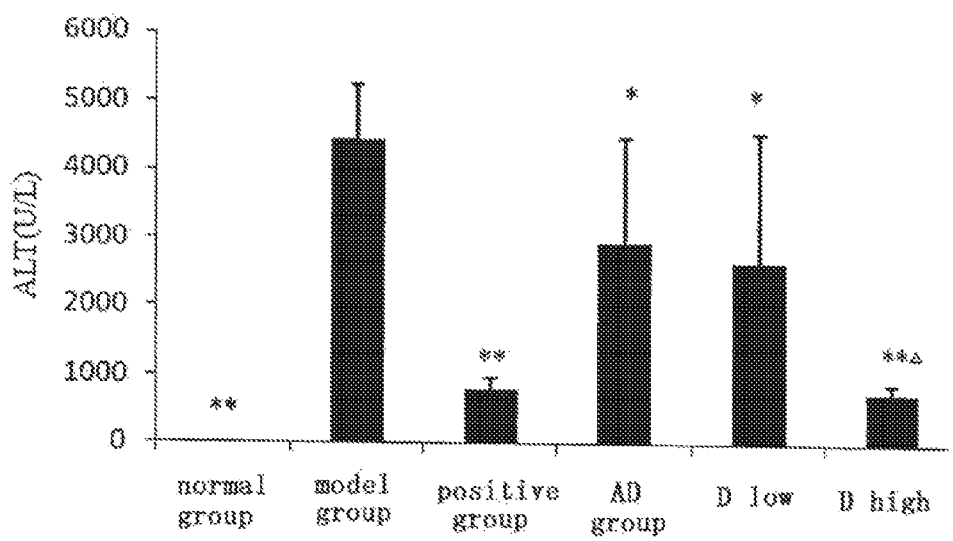
FIG. 6 shows comparison of test results for compound D and AD against ALT activity in serum of mice with ConA induced liver damage.
Figure 7:
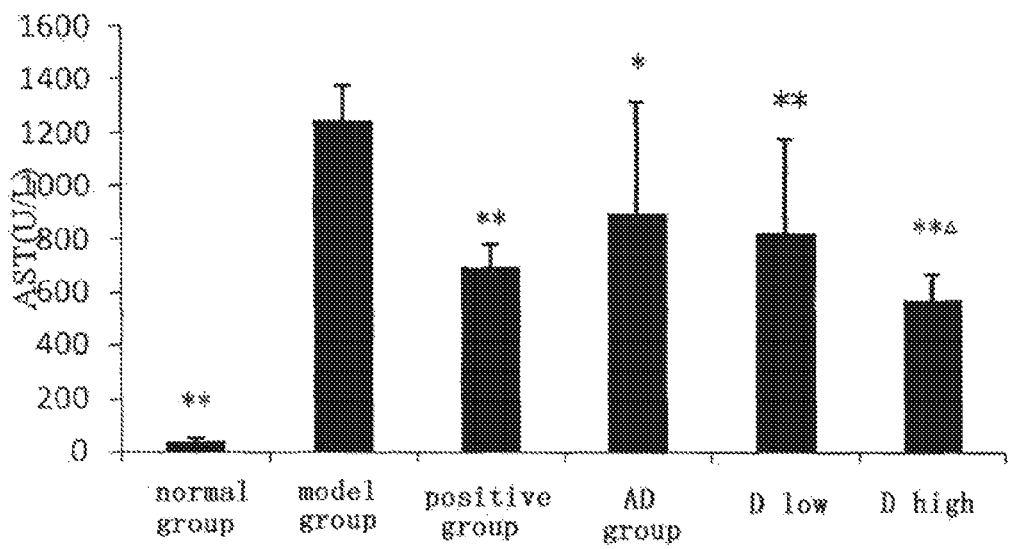
FIG. 7 shows comparison of test results for compound D and AD against AST activity in serum of mice with ConA induced liver damage.
Figure 8:
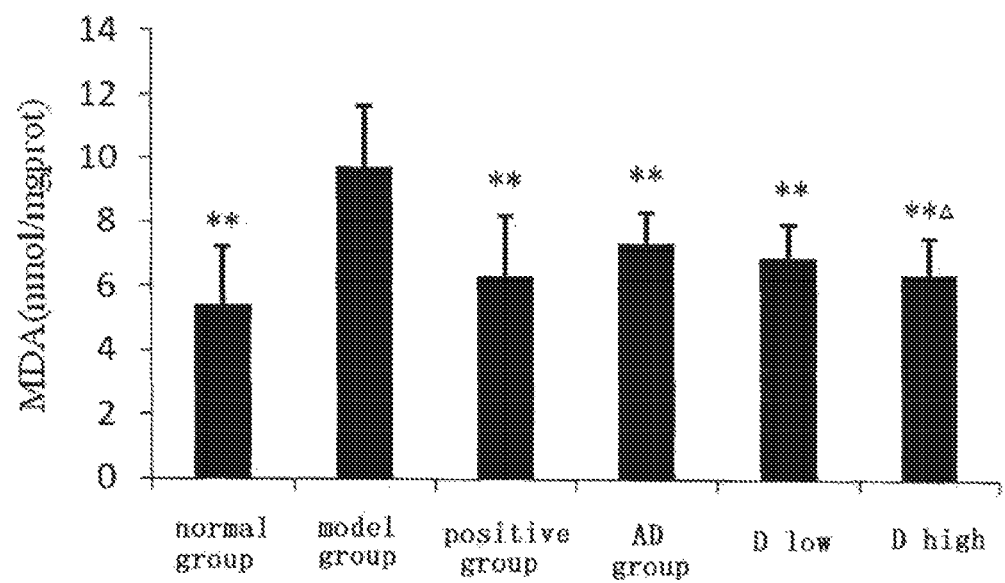
FIG. 8 shows comparison of test results for compound D and AD against MDA content in liver homogenate of mice with ConA induced liver damage.
Figure 9:
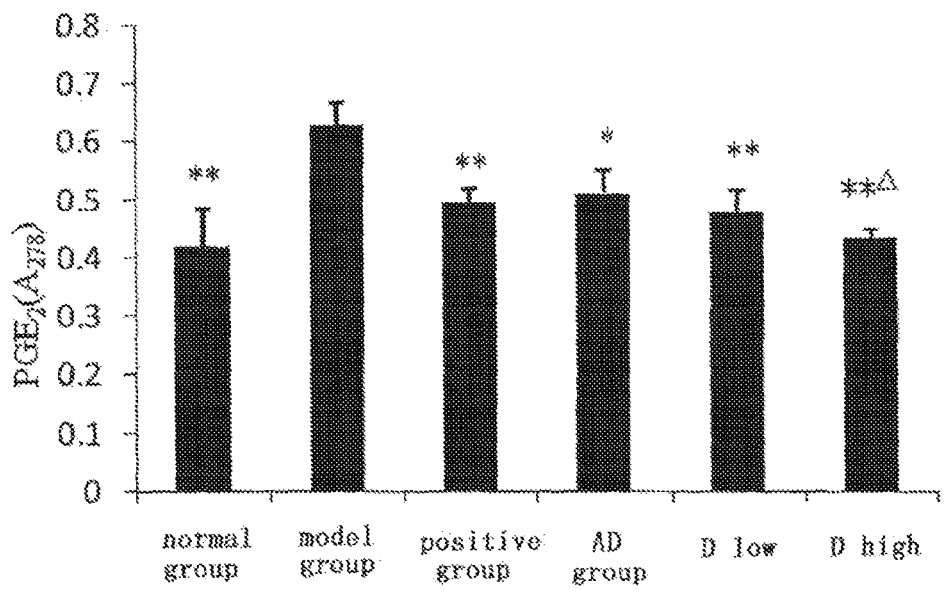
FIG. 9 shows comparison of test results for compound D and AD against $PGE_2$ content in liver homogenate of mice with ConA induced liver damage.

HE staining result of liver histopathologic section is shown in FIG. 5. In normal group, the structure of hepatic lobules is integral, liver cells are in radical arrangement with central vein in center, no degeneration or hepatonecrosis is observed, and no sinus hepaticus abnormality is observed. In model group, the mice liver lobule is damaged severely, showing swelling liver cells, loose cytoplasm, granular degeneration and vacuolar degeneration; the occurrence of dilated congestion in sinus hepaticus, nucleus shrinking or disappearing in a portion of liver cells, and the formation of obvious spotted and focal necrosis. In AD group, the liver cells are slightly swelled and loosed, a portion of liver cells show spotted necrosis and degeneration, no focal necrosis involving massive liver cells is observed. In compound A group, there is no observation of extravasated blood in sinus hepaticus, liver cells show slightly granular degeneration and vacuolar degeneration, and no spotted and focal necrosis region is observed.

Example 2

In ConA Induced Immunological Liver Damage Model, 15-p-chlorobenzylidene-3,19-nicotinate-14-deoxy-11,12-dehydroandrographolide Shows Obvious Protective Effect Against Liver Damage 1 Experimental Methods Kunming mice of clean grade (male, weight 20±2 g) are randomly divided into normal group, model group, bifendate (Zhejiang Wanbang Pharmaceutical Co., Ltd) positive control group (200 mg/kg), AD group (0.88 mmol/kg), low dosage group (0.66 mmol/kg) and high dosage (0.88 mmol/kg) group of compound D. ALT, AST, and MDA assay kits are purchased from Nanjing Jiancheng Bioengineering Institute. Other agents, drugs and experimental methods are the same as in EXAMPLE 1.

2 Experimental Results

The effect of compound D on ALT and AST activities in mice serum and MDA and $PGE_2$ content in liver homogenate are shown in FIGS. 6-9. In low dosage (P<0.05) group and high dosage (P<0.01) group of compound D, the ALT and AST activities in mice serum notably decreased comparing to model group. Low and high dosages of compound D can both significantly reduce the MDA and $PGE_2$ contents in liver homogenate (P<0.01). High dosage group has $PGE_2$ content close to that of normal group. Comparing with AD group, high dosage group (0.88 mmol/kg) of compound D has obviously increased abilities to lower the enzymes and to prevent liver lipid peroxidation (P<0.05).

In summary, compound D has significant protective effect against liver damage induced by ConA, and is better than the parent compound AD.

Example 3

Tests on the In Vitro Anti-BVDV Activity of Andrographolide Derivatives

1 Cell Culture and Drug Treatment

Pharmaceutical effects of drugs of the invention against cytopathy caused by inoculation of BVDV virus are investigated using MDBK (NBL-1) cells (purchased from Chinese Academy of Science's Shanghai Center for Type Culture Collection) and bovine viral diarrhea virus (BVDV-AV69) (purchased from China Institute of Veterinary Drugs Control). Ribavirin (R; Henan RunHong Pharmaceutical Co., Ltd; batch number: E0909604) is used as positive drug control. MDBK cells are prepared as a suspension ($1 \times 10^5$/mL) in RPMI1640 culture medium which contains 10% in volume fetal bovine serum (Zhejiang Tianhang Biotechnology Co., Ltd; batch number: 100524), 100 µg/mL streptomycin (Shenzheng Huayao Nanfang Pharmaceutical Co., Ltd; batch number: N09081), 100 U/mL penicillin (North China Pharmaceutical Co., Ltd; batch number: E0909604), and are seeded in 96 well plates (Costar, US) at 200 µL/well, placed in an incubator (Binder, Germany) at 37° C. with 5% $CO_2$ to culture the cell. In 24 h when cells grow into a single layer, virus solution of 100 $TCID_{50}$ ($TCID_{50}=10^{-2.5}$) is added and incubated for 1.5 h. Maintenance medium with the drug is added at 200 µL/well after 3×PBS washes.

2 MTT Assay for Cytotoxicity

Figure 10:
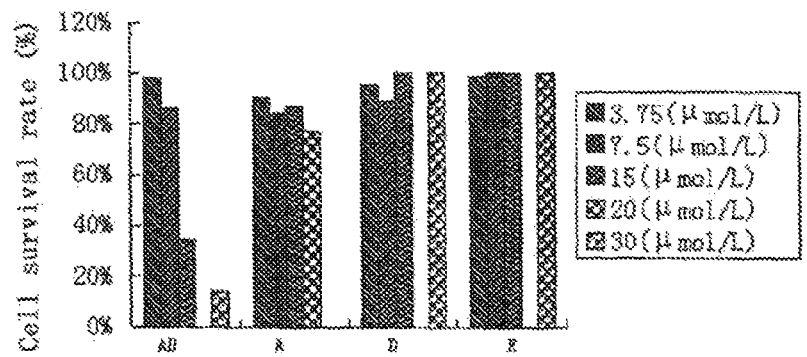
FIG. 10 shows outcome plot for cytotoxic effect of compound A, D and E against MDBK.

After digestion by trypsin and counting of healthily growing MDBK cells, the cells at $7 \times 10^4$/mL are added into 96 well plates at 200 µL/well, placed in an incubator at 37° C. with 5% $CO_2$ for 24 h. The drug-containing medium is added and further incubated for 48 h. MTT is added (5 mg/mL) at 20 µL/well and cultured for 4 h, the supernatant is discarded and 150 µL DMSO is added, then the plate is shaken for 10 minutes and the absorbance is determined using a microplate reader using the wavelength 570 nm and a reference wavelength 450 nm. The cell survival rate is calculated after treatment of compounds: cell survival rate (%)=drug group A value/cell control group A value×100%, and the results are shown in FIG. 10. Cell proliferation inhibition rate (%)=100%−survival rate (%), half maximal (50%) toxic concentration ($TC_{50}$) is calculated according to Reed-Muench method.

3 CPE Observation of Pharmaceutical Effects of Drugs on Cytopathy

Figure 11:
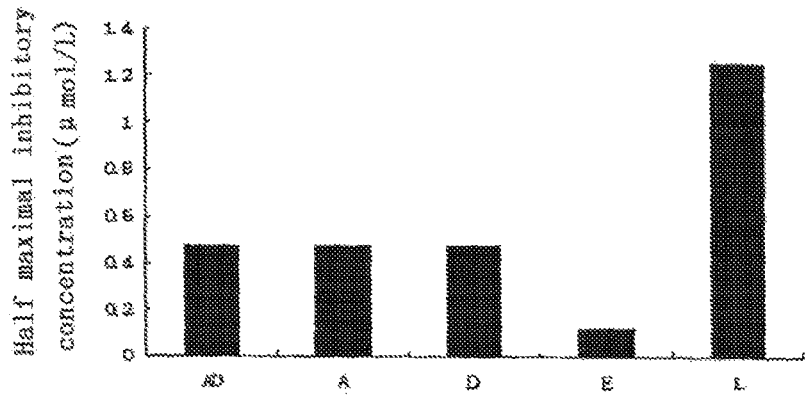
FIG. 11 shows half maximal inhibitory concentration of compound A, D and E against virus induced cytopathy.
Figure 12:
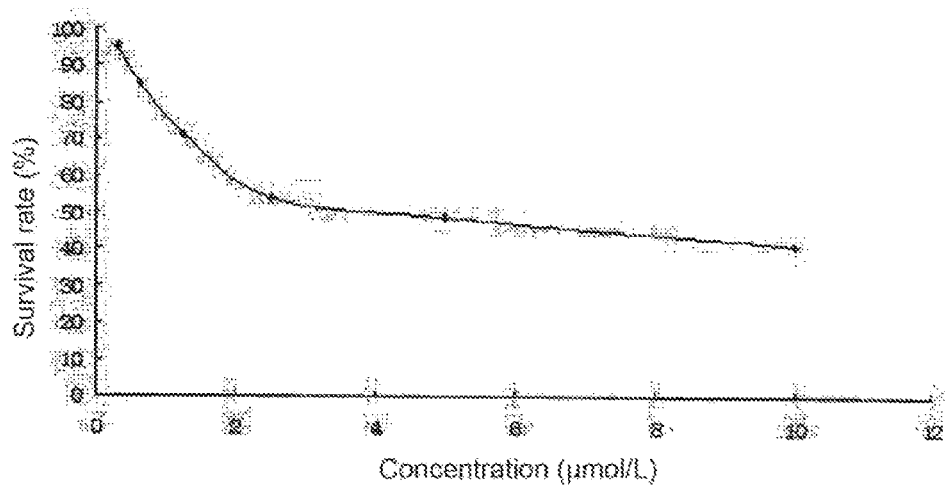
FIG. 12 shows outcome plot for cytotoxic effect of the positive drug ribavirin against MDBK.
Figure 13:
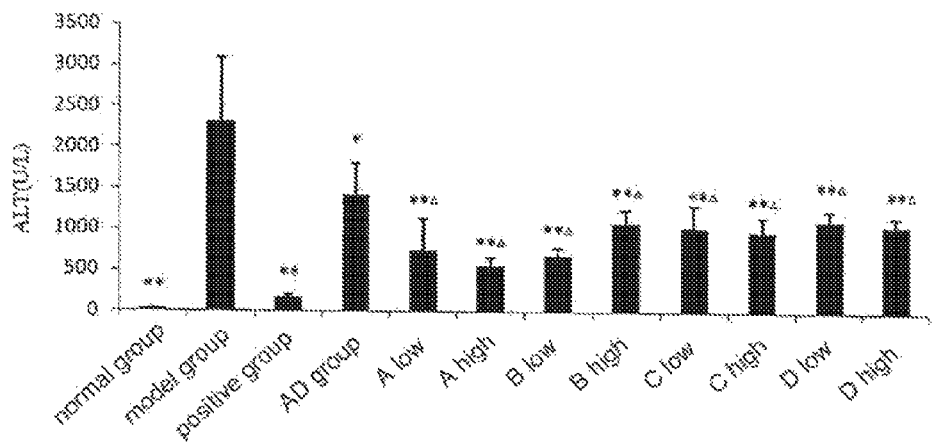
FIG. 13 shows comparison of test results for compound A, B, C, D and AD against ALT activity in serum of mice with carbon tetrachloride induced liver damage.
Figure 14:
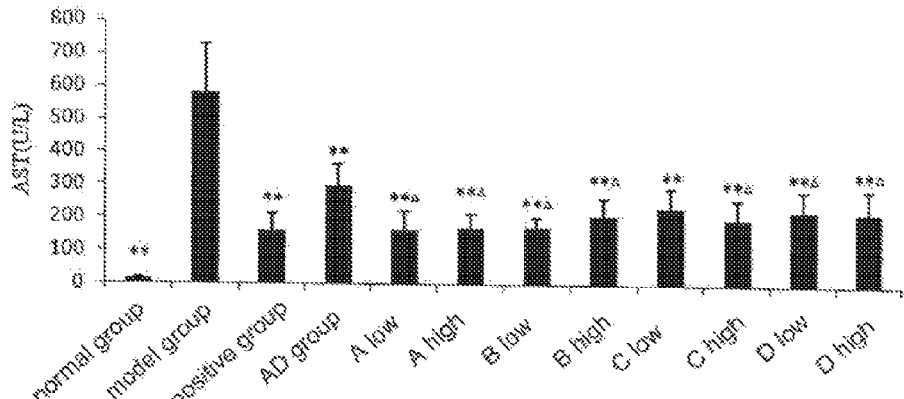
FIG. 14 shows comparison of test results for compound A, B, C, D and AD against AST activity in serum of mice with carbon tetrachloride induced liver damage.
Figure 15:
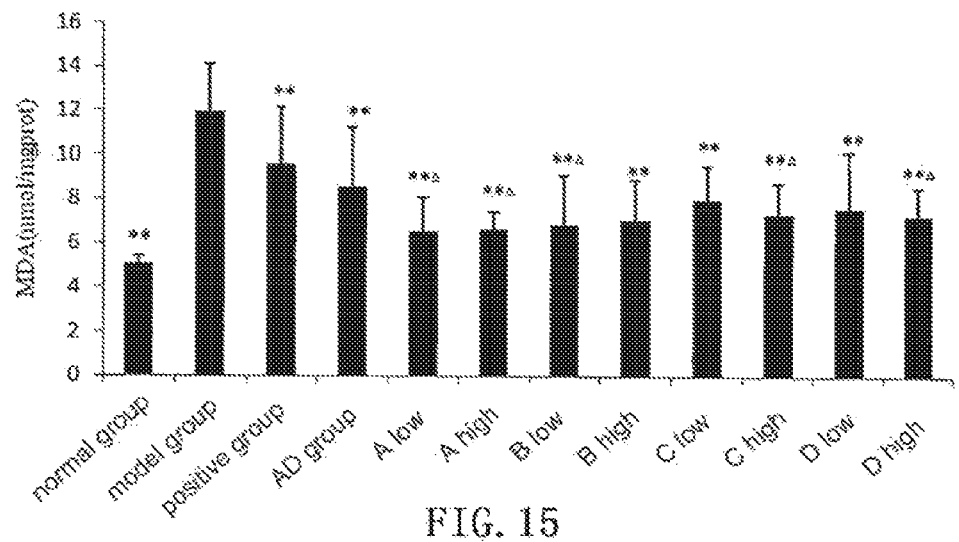
FIG. 15 shows comparison of test results for compound A, B, C, D and AD against MDA content in liver homogenate of mice with carbon tetrachloride induced liver damage.
Figure 16:
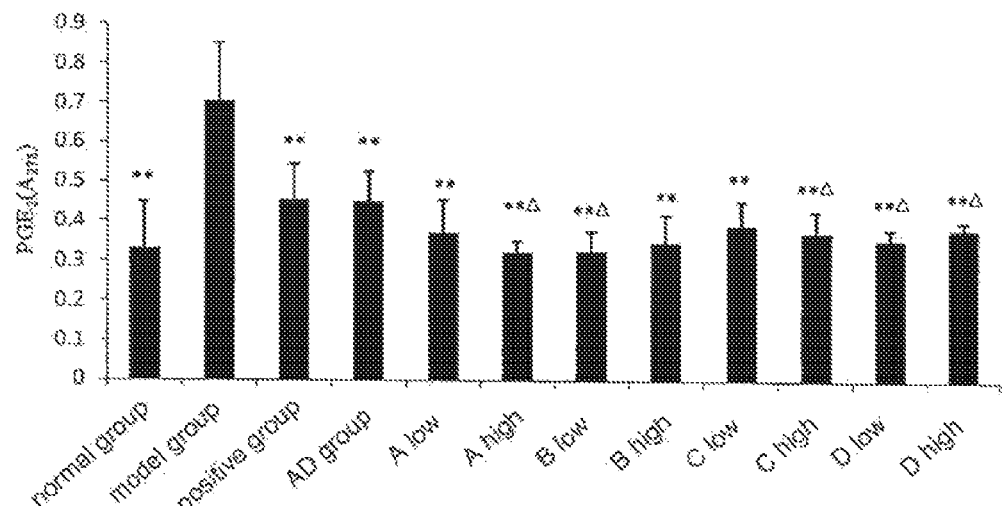
FIG. 16 shows comparison of test results for compound A, B, C, D and AD against $PGE_2$ content in liver homogenate of mice with carbon tetrachloride induced liver damage.

After digestion of MDBK cells with trypsin, cells with a concentration of $1 \times 10^5$/mL are seeded into 96 well plates at 200 µL/well, placed in an incubator at 37° C. with 5% $CO_2$ for 24 h. After growing into a single layer, cells are attacked using 100 $TCID_{50}$ ($TCID_{50}=10^{-2.5}$) virus and incubated for 1.5 h. The virus-containing maintenance medium is discarded, and cells are washed with PBS, followed by addition of drug-containing maintenance medium with different concentrations, and incubation in 5% $CO_2$ at 37° C. Normal cell control, virus control, drug treatment and ribavirin treatment groups are set. The cytopathy developing status is recorded everyday by observing under an inverted microscope. The lowest concentrations of the present compounds and the positive drug corresponding to about 50% pathological inhibitory rate are shown in FIG. 11. The therapy index (TI) ($TC_{50}/IC_{50}$) is calculated and shown in Table 1.

TABLE 1

TI values of compound A, D, E and the positive drug

| Compound | TI value |
| --- | --- |
| AD | 14.4 |
| Compound A | >127.6 |
| Compound D | >127.6 |
| Compound E | >250 |
| Ribavirin(R) | 4 |

4 Experimental Results

Before antiviral experiment of test compounds, it is necessary to determine the lowest non-toxic concentration of the test compound to MDBK cells to make sure that the compound will not affect the normal activity of MDBK cells when exerting its function on BVDV virus. The compounds A, D and E do not show obvious cytotoxcity to MDBK cells at the range of concentration 0-7.5 μmol/L after 48 h, wherein compound E at an increased concentration of 30 μmol/L shows no cytotoxcity either. Compounds A, D and E, especially compound E, show better antiviral effect than AD. TI values show that AD and compounds A, D and E all have higher TI than the positive drug, whereas compound E has the highest TI.

In summary, pharmaceutical effects of the compounds A, D and E against cytopathy caused by virus are all better than ribavirin, and much safer.

Example 4

In Carbon Tetrachloride Induced Liver Damage Model, Compound A, B and AD Show Obvious Protective Effect Against Liver Damage 1 Experimental Methods Kunming mice of clean grade (male, weight 20±2 g), after adaptively fed for 3 days, are randomly divided into normal group, model group, bifendate positive control group (200 mg/kg), AD group (0.88 mmol/kg), low dosage group (0.66 mmol/kg) and high dosage group (0.88 mmol/kg) of compound A, B, C and D, with 8 mice in each group. Positive group and each test group are intragastrically given with respective suspension prepared with 0.5% CMC-Na, and normal group and model group are given with 0.5% CMC-Na. The drugs are given for 3 days, and 1 h after the last administration, all mice except those in the normal group are intraperitoneally injected with a single dose of 0.3% carbon tetrachloride in peanut oil (0.1 mL/10 g). After 16 h, the eyeball of the mice in each group is enucleated to collect blood, which is centrifuged at 3000 rpm for 15 min to separate serum. ALT and AST activities are tested respectively (Nanjing Jiancheng Bioengineering Institute). The left lobe of liver is taken to prepare 10% homogenate using physiological saline, MDA (Nanjing Jiancheng Bioengineering Institute) and $PGE_2$ contents are determined. Experimental data are expressed as average±standard deviation ($\bar{X}±s$), analyzed with SPSS 11.5 statistic software, with P<0.05 meaning there is a significant difference. Other agents, drugs and experimental methods are the same as in EXAMPLE 1.

2 Experimental Results

The effects of each group on ALT and AST activities in serum and MDA and $PGE_2$ contents in liver homogenate are shown in FIGS. 13-16. As shown in the results, compound A, B, C and D all can notably suppress the increase of ALT and AST activity in serum of mice with liver damage induced by carbon tetrachloride (P<0.01). Comparing to AD group, the magnitude of decrease in enzyme activities is significantly better in low dosage groups (0.66 mmol/kg) and high dosage groups (0.88 mmol/kg) of compound A, B, C and D (P<0.05).

Compound A, B, C and D can all effectively reduce the levels of MDA and $PGE_2$ in liver homogenate from mice with liver damage, showing a difference with extraordinary significance (P<0.01). Comparing to AD group, the low (0.66 mmol/kg) and high dosage (0.88 mmol/kg) groups of compound A, low dosage group of compound B, high dosage groups (0.88 mmol/kg) of compound C and D have stronger ability to reduce the lipid peroxide level in liver homogenate (P<0.05). $PGE_2$ content, in high dosage groups of compound A and C, low dosage group of compound B and low/high dosage group of compound D, are notably lower than that in AD group (P<0.05)

In summary, compound A, B, C and D have protective effect against liver damage induced by carbon tetrachloride, and are better than the parent compound AD.

Example 5

In Ethanol Induced Liver Damage Model, Compound A, B, C and D Show Obvious Protective Effect Against Liver Damage 3 Experimental Methods Kunming mice of clean grade (male, weight 20±2 g), after adaptively fed for 3 days, are randomly divided into normal group, model group, bifendate positive control group (200 mg/kg), AD group (0.88 mmol/kg), low (0.44 mmol/kg), median (0.66 mmol/kg) and high (0.88 mmol/kg) dosage groups of compound A, and median (0.66 mmol/kg) and high (0.88 mmol/kg) dosage groups of compound B, with 8 mice in each group. Positive group and each test group are intragastrically given with respective suspension prepared with 0.5% CMC-Na, and normal group and model group are given with 0.5% CMC-Na. The drugs are given for 3 days, and 1 h after the last administration, all mice except those in the normal group are intragastrically administrated with a single dose of 50% EtOH (1.2 mL/10 g). After 16 h, the eyeball of the mice in each group is enucleated to collect blood, which is centrifuged at 3000 rpm for 15 min to separate serum. ALT and AST activities are tested respectively (Nanjing Jiancheng Bioengineering Institute). The left lobe of liver is taken to prepare 10% homogenate using physiological saline, MDA (Nanjing Jiancheng Bioengineering Institute) content is determined. Experimental data are expressed as average±standard deviation ($\bar{X}±s$), analyzed with SPSS 11.5 statistic software, with P<0.05 meaning there is a significant difference. Other agents, drugs and experimental methods are the same as in EXAMPLE 1.

4 Experimental Results

Figure 17:
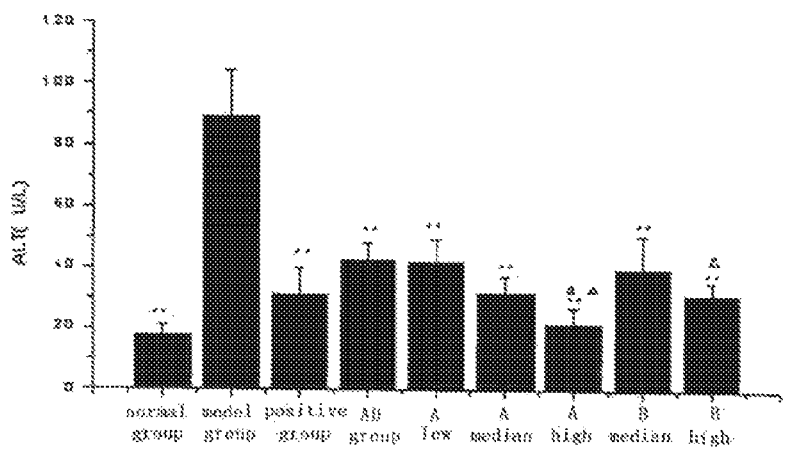
FIG. 17 shows comparison of test results for compound A, B and AD against ALT activity in serum of mice with ethanol induced liver damage.
Figure 18:
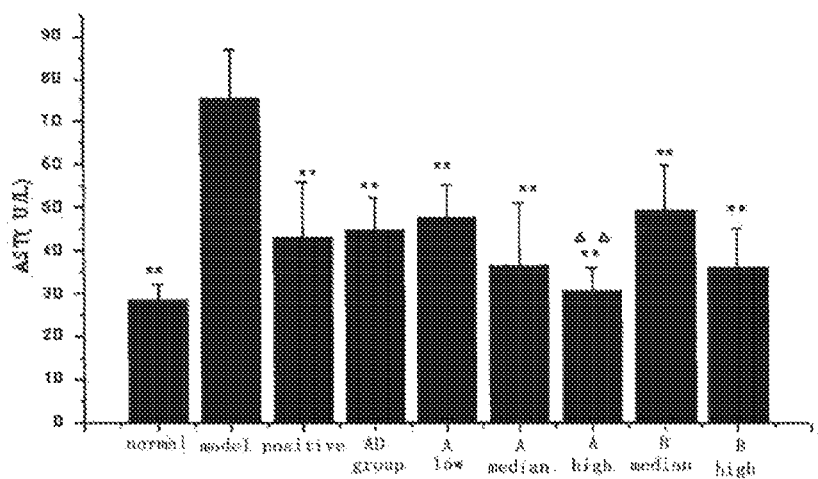
FIG. 18 shows comparison of test results for compound A, B and AD against AST activity in serum of mice with ethanol induced liver damage.
Figure 19:
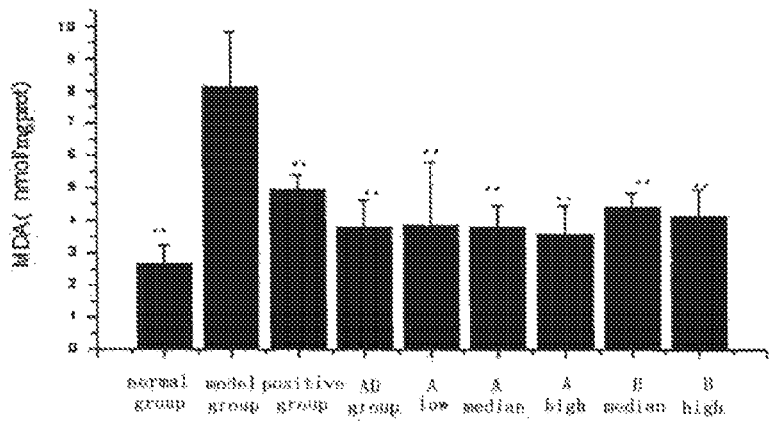
FIG. 19 shows comparison of test results for compound A, B and AD against MDA content in liver homogenate of mice with ethanol induced liver damage.

The effects of each group on ALT and AST activities in serum and MDA content in liver homogenate are shown in FIGS. 17-19. As revealed by the results, compound A and B both can effectively suppress ALT and AST activities in serum of mice with liver damage induced by ethanol, and suppress the increase of MDA content in liver homogenate (P<0.01). The ALT activity decreasing magnitudes in the high dosage (0.88 mmol/kg) group of compound A (P<0.01) and B (P<0.05) are notably larger than in AD group, and the AST activity decreasing magnitude in the high dosage (0.88 mmol/kg) group of compound A (P<0.01) is notably larger than in AD group. Compound A and B both can effectively reduce the MDA content (P<0.01) in liver homogenate of mice with liver damage.

In summary, compound A and B have protective effect against liver damage induced by ethanol, and are better than the parent compound AD.

Example 6

Using Carbon Tetrachloride Induced Chemical Liver Damage Model and ConA Induced Immunological Liver Damage Model, Protective Effect of Compound E Against Liver Damage is Investigated 1 Experimental Methods In experimental investigation of both models, the following grouping method is used: Kunming mice of clean grade (male, weight 20±2 g) are randomly divided into normal group, model group, bifendate group (200 mg/kg), AD group (0.88 mmol/kg), low dosage group (0.66 mmol/kg) and high dosage group (0.88 mmol/kg) of compound E, with 8 mice in each group. Other agents, drugs and experimental methods are the same as in EXAMPLE 1 and in EXAMPLE 4, respectively.

2 Experimental Results

Figure 20:
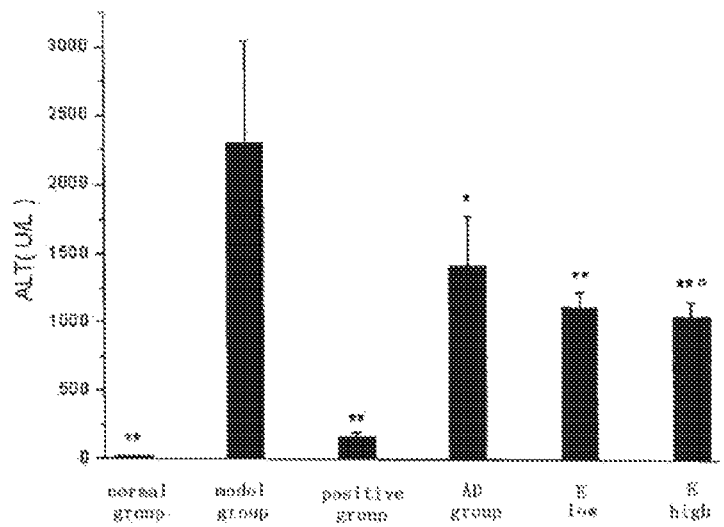
FIG. 20 shows comparison of test results for compound E and AD against ALT activity in serum of mice with carbon tetrachloride induced liver damage.
Figure 21:
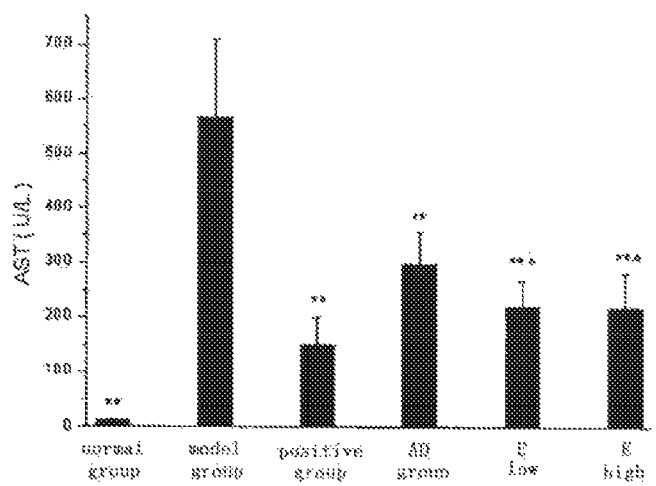
FIG. 21 shows comparison of test results for compound E and AD against AST activity in serum of mice with carbon tetrachloride induced liver damage.
Figure 22:
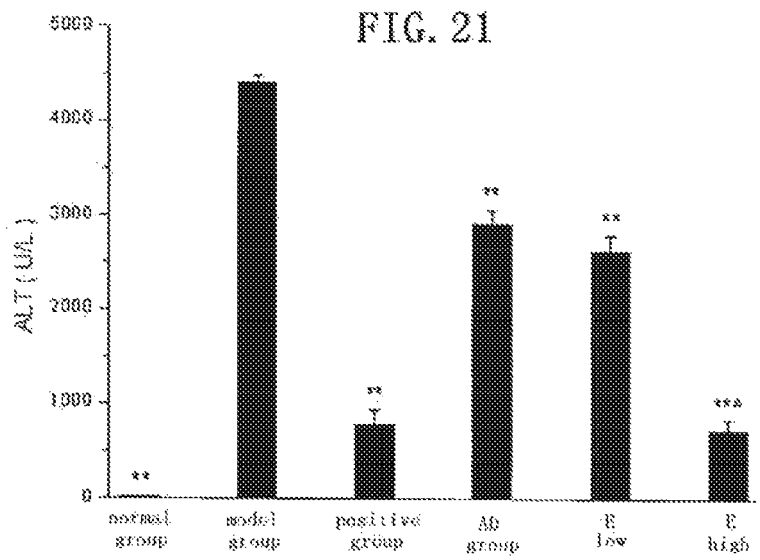
FIG. 22 shows comparison of test results for compound E and AD against ALT activity in serum of mice with ConA induced liver damage.
Figure 23:
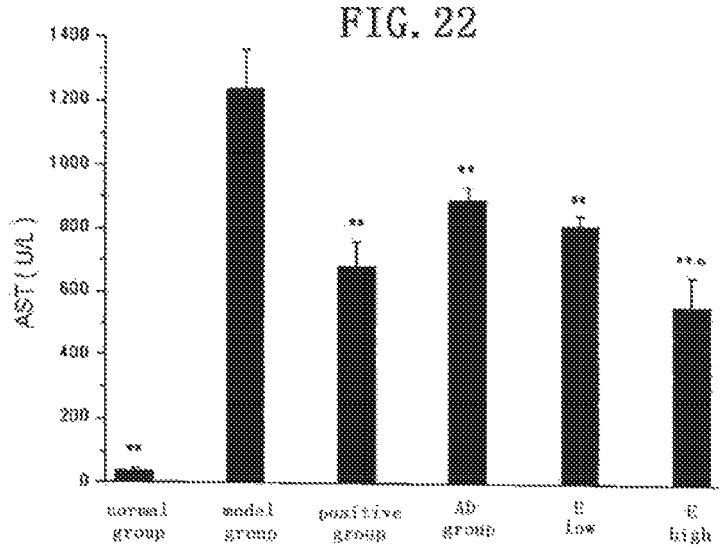
FIG. 23 shows comparison of test results for compound E and AD against AST activity in serum of mice with ConA induced liver damage.

In study of the chemical liver damage induced by carbon tetrachloride, the effects of each group on ALT and AST activities in serum are shown in FIGS. 20-21. Comparing with model group, the ALT and AST activities in mice serum of low/high dosage group of compound E notably decrease (P<0.01), and comparing with AD group, AST activity and ALT activity of high dosage group are notably lower (P<0.05). In study of the immunological liver damage induced by ConA, the effects of each group on ALT and AST activities are shown in FIGS. 22-23. It is shown by results that the ALT and AST activities in mice serum of low/high dosage group of compound E notably decrease comparing to model group (P<0.01), and are notably lower than AD group (P<0.05).

In summary, compound E has significant protective effect against liver damage induced by carbon tetrachloride and ConA, and is much better than the parent compound AD.

What is claimed is:

1. A method of treating liver damage, comprising administering a dosage form comprising a 15-benzylidene-14-deoxy-11,12-dehydroandrographolide derivative having a structure as shown in Formula 1,

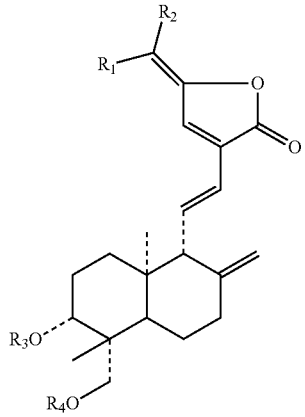

Formula 1 selected from the group consisting of the following:
A: $R_1$=H, $R_2$=4-Cl—$C_6H_4$, $R_3$=$R_4$=H;
B: $R_1$=H, $R_2$=$C_6H_5$, $R_3$=$R_4$=H;
C: $R_1$=H, $R_2$=3-Br—$C_6H_4$, $R_3$=$R_4$=H;
D: $R_1$=H, $R_2$=4-Cl—$C_6H_4$, $R_3$=$R_4$=$COR_5$, $R_5$=3-pyridyl;
E: $R_1$=H, $R_2$=4-Cl—$C_6H_4$, $R_3$=$R_4$=$COR_5$, $R_5$=$CH_2CH_2COOH$.

2. The method of claim 1, wherein the liver damage is caused by a virus infection or a drug.

3. The method of claim 1, wherein the dosage form further comprising a pharmaceutically acceptable auxiliary and/or additive.

4. The method of claim 3, wherein the dosage form is an oral form or an injectable form.

5. The method of claim 4, wherein the oral form is a tablet, pill, capsule, granule or syrup.

6. The method of claim 4, wherein the injectable form is an injection or a lyophilized powder for injection.

* * * * *